(12) United States Patent
Radu et al.

(10) Patent No.: US 9,685,613 B2
(45) Date of Patent: Jun. 20, 2017

(54) ELECTROACTIVE MATERIALS

(75) Inventors: Nora Sabina Radu, Landenberg, PA (US); Adam Fennimore, Wilmington, DE (US)

(73) Assignee: E I DU PONT DE NEMOURS AND COMPANY, Wilmington, DE (US)

(*) Notice: Subject to any disclaimer, the term of this patent is extended or adjusted under 35 U.S.C. 154(b) by 656 days.

(21) Appl. No.: 13/990,800

(22) PCT Filed: Dec. 19, 2011

(86) PCT No.: PCT/US2011/065834
§ 371 (c)(1),
(2), (4) Date: May 31, 2013

(87) PCT Pub. No.: WO2012/087930
PCT Pub. Date: Jun. 28, 2012

(65) Prior Publication Data
US 2013/0248847 A1    Sep. 26, 2013

Related U.S. Application Data

(60) Provisional application No. 61/424,840, filed on Dec. 20, 2010.

(51) Int. Cl.
*H01L 51/50* (2006.01)
*H01L 51/00* (2006.01)
(Continued)

(52) U.S. Cl.
CPC .......... *H01L 51/006* (2013.01); *C07C 211/61* (2013.01); *C08G 61/12* (2013.01);
(Continued)

(58) Field of Classification Search
None
See application file for complete search history.

(56) References Cited

U.S. PATENT DOCUMENTS 5,840,217 A    11/1998    Lupo et al.
6,670,645 B2    12/2003    Grushin et al.
(Continued)

FOREIGN PATENT DOCUMENTS

DE    102009012163 A1    9/2010
DE    102010010481 A1    9/2011
(Continued)

OTHER PUBLICATIONS

Machine translation for JP 2007-110097 A (publication date: Apr. 2007).*
(Continued)

*Primary Examiner* — Dawn Garrett

(57) ABSTRACT

There is disclosed a compound having Formula I

Formula I

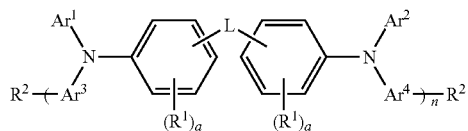

In Formula I:
 Ar$^1$ through Ar$^4$ are the same or different and are aryl groups;
 L is a spiro group, an adamantyl group, bicyclic cyclohexyl, deuterated analogs thereof, or substituted derivatives thereof;
 R$^1$ is the same or different at each occurrence and is D, F, alkyl, aryl, alkoxy, silyl, or a crosslinkable group, where adjacent R$^1$ groups can be joined together to form an aromatic ring;
(Continued)

$R^2$ is the same or different at each occurrence and is H, D, or halogen;

a is the same or different at each occurrence and is an integer from 0-4; and n is an integer greater than 0.

20 Claims, 2 Drawing Sheets

(51) Int. Cl.
    *C09K 11/06* (2006.01)
    *C07C 211/61* (2006.01)
    *C08G 61/12* (2006.01)

(52) U.S. Cl.
    CPC .......... *C09K 11/06* (2013.01); *H01L 51/0035* (2013.01); *H01L 51/0059* (2013.01); *C07C 2103/94* (2013.01); *C08G 2261/3162* (2013.01); *C08G 2261/3424* (2013.01); *C08G 2261/512* (2013.01); *C08G 2261/5222* (2013.01); *C08G 2261/95* (2013.01)

(56) References Cited

U.S. PATENT DOCUMENTS

| | | | | |
|---|---|---|---|---|
| 6,747,287 | B1* | 6/2004 | Toguchi | H01L 51/0056 257/40 |
| 2001/0033944 | A1* | 10/2001 | Onikubo | C07C 211/54 428/690 |
| 2003/0118866 | A1* | 6/2003 | Oh | H01L 51/0058 428/690 |
| 2004/0102577 | A1 | 5/2004 | Hsu et al. | |
| 2004/0127637 | A1 | 7/2004 | Hsu et al. | |
| 2005/0184287 | A1 | 8/2005 | Herron et al. | |
| 2005/0205860 | A1 | 9/2005 | Hsu et al. | |
| 2007/0262703 | A1* | 11/2007 | Tsai | C07C 211/61 313/503 |
| 2008/0191617 | A1* | 8/2008 | Chae | H01L 51/005 313/504 |
| 2009/0081357 | A1* | 3/2009 | Taka | B82Y 20/00 427/66 |
| 2012/0003485 | A1* | 1/2012 | Habich | H01L 51/5088 428/447 |
| 2012/0326141 | A1 | 12/2012 | Pflumm | |
| 2013/0248848 | A1* | 9/2013 | Radu | H01L 51/0018 257/40 |

FOREIGN PATENT DOCUMENTS

| | | |
|---|---|---|
| EP | 676461 A2 | 8/2002 |
| EP | 1289028 A1 | 3/2003 |
| EP | 1624500 A1 | 2/2006 |
| EP | 2180029 A1 | 4/2010 |
| JP | 2007-110097 A * | 4/2007 |
| JP | 2007110097 A | 4/2007 |
| JP | 2011113650 A | 6/2011 |
| JP | 2011173973 A | 9/2011 |
| JP | 2012023266 A | 2/2012 |
| WO | 02051958 A1 | 7/2002 |
| WO | 03008424 A1 | 1/2003 |
| WO | 03040257 A1 | 5/2003 |
| WO | 03063555 A1 | 7/2003 |
| WO | 03091688 A2 | 11/2003 |
| WO | 2004016710 A1 | 2/2004 |
| WO | 2005052027 A1 | 6/2005 |
| WO | 2007145979 A3 | 4/2008 |

OTHER PUBLICATIONS

"Illustrated Glossary of Organic Chemistry—Divalent." Illustrated Glossary of Organic Chemistry—Divalent. N.p., n.d. Web. Aug. 29, 2016.*

Gustafsson et al., "Flexible Light-Emitting Diodes Made From Soluble Conducting Polymers," Nature, 1992, vol. 357, pp. 477-479.

Wang, "Photoconductive Materials," Kirk-Othmer Encyclopedia of Chemical Technology, Fourth Edition, 1996, vol. 18, pp. 837-860.

International Search Report, European Patent Office, Rijswijk in PCT/US2011/065834, PCT Counterpart of the Present U.S. Appl. No. 13/990,800, Guillaume Dunet Authorized Officer, Aug. 14, 2012.

* cited by examiner

US 9,685,613 B2

ELECTROACTIVE MATERIALS

RELATED APPLICATION DATA

This application claims priority under 35 U.S.C. §119(e) from U.S. Provisional Application No. 61/424,840 filed on Dec. 20, 2010, which is incorporated by reference herein in its entirety.

BACKGROUND INFORMATION

Field of the Disclosure

The present disclosure relates to novel electroactive compounds. The disclosure further relates to electronic devices having at least one layer comprising such an electroactive compound.

Description of the Related Art

In organic electronic devices, such as organic light emitting diodes ("OLED"), that make up OLED displays, the organic electroactive layer is sandwiched between two electrical contact layers in an OLED display. In an OLED the organic electroactive layer emits light through the light-transmitting electrical contact layer upon application of a voltage across the electrical contact layers.

It is well known to use organic electroluminescent compounds as the electroactive component in light-emitting diodes. Simple organic molecules, conjugated polymers, and organometallic complexes have been used.

Devices that use electroluminescent materials frequently include one or more charge transport layers, which are positioned between an electroactive (e.g., light-emitting) layer and a contact layer (hole-injecting contact layer). A device can contain two or more contact layers. A hole transport layer can be positioned between the electroactive layer and the hole-injecting contact layer. The hole-injecting contact layer may also be called the anode. An electron transport layer can be positioned between the electroactive layer and the electron-injecting contact layer. The electron-injecting contact layer may also be called the cathode.

There is a continuing need for electroactive materials for use in electronic devices.

SUMMARY

There is provided a compound having Formula I

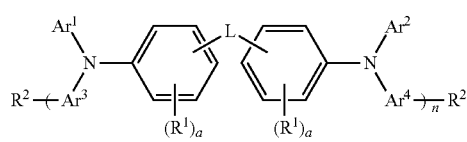

Formula I wherein:
  Ar$^1$ through Ar$^4$ are the same or different and are aryl groups;
  L is selected from the group consisting of a spiro group, an adamantyl group, bicyclic cyclohexyl, deuterated analogs thereof, and substituted derivatives thereof;
  R$^1$ is the same or different at each occurrence and is selected from the group consisting of D, F, alkyl, aryl, alkoxy, silyl, and a crosslinkable group, where adjacent R$^1$ groups can be joined together to form an aromatic ring;
  R$^2$ is the same or different at each occurrence and is selected from the group consisting of H, D, and halogen;
  a is the same or different at each occurrence and is an integer from 0-4; and
  n is an integer greater than 0.

There is also provided an electronic device having at least one layer comprising the above compound.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

Figure 1:
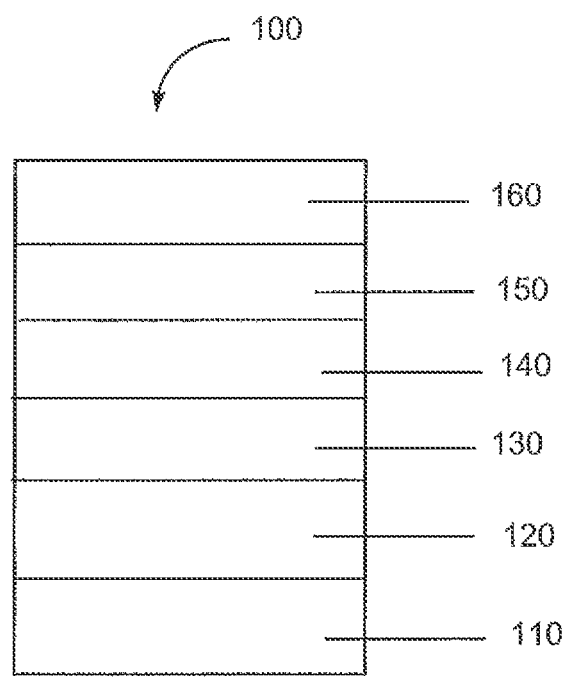
FIG. 1 includes an illustration of one example of an organic electronic device.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

There is provided a compound having Formula I

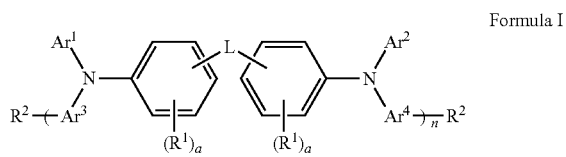

Formula I wherein:
  Ar$^1$ through Ar$^4$ are the same or different and are aryl groups;
  L is selected from the group consisting of a spiro group, an adamantyl group, bicyclic cyclohexyl, deuterated analogs thereof, and substituted derivatives thereof;
  R$^1$ is the same or different at each occurrence and is selected from the group consisting of D, F, alkyl, aryl, alkoxy, silyl, and a crosslinkable group, where adjacent R$^1$ groups can be joined together to form an aromatic ring;
  R$^2$ is the same or different at each occurrence and is selected from the group consisting of H, D, and halogen;
  a is the same or different at each occurrence and is an integer from 0-4; and
  n is an integer greater than 0.

There is further provided a compound having Formula II

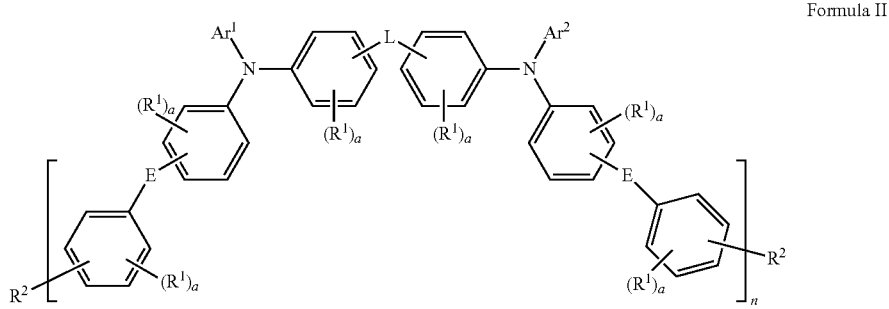

Formula II wherein:
Ar$^1$ and Ar$^2$ are the same or different and are aryl groups;
L is selected from the group consisting of a spiro group, an adamantyl group, bicyclic cyclohexyl, deuterated analogs thereof, and substituted derivatives thereof;
E is the same or different at each occurrence and is selected from the group consisting of a single bond, C(R$^3$)$_2$, C(R$^4$)$_2$C(R$^4$)$_2$, O, Si(R$^3$)$_2$, Ge(R$^3$)$_2$;
R$^1$ is the same or different at each occurrence and is selected from the group consisting of D, F, alkyl, aryl, alkoxy, silyl, and a crosslinkable group, where adjacent R$^1$ groups can be joined together to form an aromatic ring;
R$^2$ is the same or different at each occurrence and is selected from the group consisting of H, D, and halogen;
R$^3$ is the same or different at each occurrence and is selected from the group consisting of alkyl and aryl, where adjacent R$^3$ groups can be joined together to form an aliphatic ring;
R$^4$ is the same or different at each occurrence and is selected from the group consisting of H, D, and alkyl;
a is the same or different at each occurrence and is an integer from 0-4; and
n is an integer greater than 0.

There is further provided a compound having Formula I

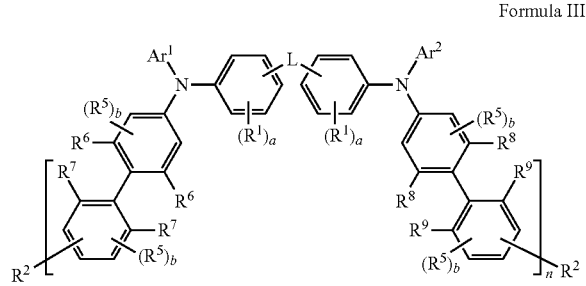

Formula III wherein:
Ar$^1$ and Ar$^2$ are the same or different and are aryl groups;
L is selected from the group consisting of a spiro group, an adamantyl group, bicyclic cyclohexyl, deuterated analogs thereof, and substituted derivatives thereof;
R$^1$ is the same or different at each occurrence and is selected from the group consisting of D, F, alkyl, aryl, alkoxy, silyl, and a crosslinkable group, where adjacent R$^1$ groups can be joined together to form an aromatic ring;

R$^2$ is the same or different at each occurrence and is selected from the group consisting of H, D, and halogen;
R$^5$ is the same or different at each occurrence and is selected from the group consisting of D, F, alkyl, aryl, alkoxy, silyl, and a crosslinkable group;
R$^6$ through R$^9$ are the same or different at each occurrence and are selected from the group consisting of H, D, F, alkyl, aryl, alkoxy, silyl, and a crosslinkable group, with the proviso that at least one of R$^6$ and R$^7$ is alkyl or silyl, and at least one of R$^8$ and R$^9$ is alkyl or silyl;
a is the same or different at each occurrence and is an integer from 0-4;
b is the same or different at each occurrence and is an integer from 0-2; and
n is an integer greater than 0.

There is further provided an electronic device having at least one layer comprising a compound having Formula I, Formula II, or Formula III.

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the Electroactive Compound, the Electronic Device, and finally Examples.

1. DEFINITIONS AND CLARIFICATION OF TERMS

Before addressing details of embodiments described below, some terms are defined or clarified.

As used herein, the term "alkyl" includes branched and straight-chain saturated aliphatic hydrocarbon groups. Unless otherwise indicated, the term is also intended to include cyclic groups. Examples of alkyl groups include methyl, ethyl, propyl, isopropyl, isobutyl, secbutyl, tertbutyl, pentyl, isopentyl, neopentyl, cyclopentyl, hexyl, cyclohexyl, isohexyl and the like. The term "alkyl" further includes both substituted and unsubstituted hydrocarbon groups. In some embodiments, the alkyl group may be mono-, di- and tri-substituted. One example of a substituted alkyl group is trifluoromethyl. Other substituted alkyl groups are formed from one or more of the substituents described herein. In certain embodiments alkyl groups have 1 to 20 carbon atoms. In other embodiments, the group has 1 to 6 carbon atoms. The term is intended to include heteroalkyl groups. Heteroalkyl groups may have from 1-20 carbon atoms.

The term "aryl" means an aromatic carbocyclic moiety, which may be a single ring (monocyclic) or multiple rings (bicyclic, or more) fused together or linked covalently. Any suitable ring position of the aryl moiety may be covalently linked to the defined chemical structure. Examples of aryl moieties include, but are not limited to, phenyl, 1-naphthyl, 2-naphthyl, dihydronaphthyl, tetrahydronaphthyl, biphenyl, anthryl, phenanthryl, fluorenyl, indanyl, biphenylenyl, acenaphthenyl, acenaphthylenyl, and the like. In some embodiments, aryl groups have 6 to 60 carbon atoms; in some embodiments, 6 to 30 carbon atoms. The term is intended to include heteroaryl groups. Heteroaryl groups may have from 4-50 carbon atoms; in some embodiments, 4-30 carbon atoms.

The term "alkoxy" is intended to mean the group —OR, where R is alkyl.

The term "aryloxy" is intended to mean the group —OR, where R is aryl.

Unless otherwise indicated, all groups can be substituted or unsubstituted. An optionally substituted group, such as, but not limited to, alkyl or aryl, may be substituted with one or more substituents which may be the same or different. Suitable substituents include D, alkyl, aryl, nitro, cyano, —N($R^7$)($R^8$), halo, hydroxy, carboxy, alkenyl, alkynyl, cycloalkyl, heteroaryl, alkoxy, aryloxy, heteroaryloxy, alkoxycarbonyl, perfluoroalkyl, perfluoroalkoxy, arylalkyl, silyl, siloxane, thioalkoxy, —S(O)$_2$—N(R')(R"), —C(=)—N(R')(R"), (R')(R")N-alkyl, (R')(R")N-alkoxyalkyl, (R')(R")N-alkylaryloxyalkyl, —S(O)$_s$-aryl (where s=0-2) or —S(O)$_s$-heteroaryl (where s=0-2). Each R' and R' is independently an optionally substituted alkyl, cycloalkyl, or aryl group. R' and R", together with the nitrogen atom to which they are bound, can form a ring system in certain embodiments. Substituents may also be crosslinking groups.

The term "charge transport," when referring to a layer, material, member, or structure is intended to mean such layer, material, member, or structure facilitates migration of such charge through the thickness of such layer, material, member, or structure with relative efficiency and small loss of charge. Hole transport materials facilitate positive charge; electron transport materials facilitate negative charge. Although light-emitting materials may also have some charge transport properties, the term "charge transport layer, material, member, or structure" is not intended to include a layer, material, member, or structure whose primary function is light emission.

The term "compound" is intended to mean an electrically uncharged substance made up of molecules that further include atoms, wherein the atoms cannot be separated from their corresponding molecules by physical means without breaking chemical bonds. The term is intended to include oligomers and polymers.

The term "crosslinkable group" or "crosslinking group" is intended to mean a group than can lead to crosslinking via thermal treatment or exposure to radiation. In some embodiments, the radiation is UV or visible.

The term "electroactive" as it refers to a layer or a material, is intended to indicate a layer or material which electronically facilitates the operation of the device. Examples of electroactive materials include, but are not limited to, materials which conduct, inject, transport, or block a charge, where the charge can be either an electron or a hole, or materials which emit radiation or exhibit a change in concentration of electron-hole pairs when receiving radiation. Examples of inactive materials include, but are not limited to, planarization materials, insulating materials, and environmental barrier materials.

The prefix "fluoro" is intended to indicate that one or more hydrogens in a group has been replaced with fluorine.

The prefix "hetero" indicates that one or more carbon atoms has been replaced with a different atom. In some embodiments, the heteroatom is O, N, S, or combinations thereof.

The term "liquid composition" is intended to mean a liquid medium in which a material is dissolved to form a solution, a liquid medium in which a material is dispersed to form a dispersion, or a liquid medium in which a material is suspended to form a suspension or an emulsion.

The term "silyl" refers to the group $R_3Si$—, where R is H, D, C1-20 alkyl, fluoroalkyl, or aryl. In some embodiments, one or more carbons in an R alkyl group are replaced with Si. In some embodiments, the silyl groups are (hexyl)$_2$Si(Me)CH$_2$CH$_2$Si(Me)$_2$- and [CF$_3$(CF$_2$)CH$_2$CH$_2$]$_2$SiMe-.

The term "siloxane" refers to the group $(RO)_3Si$—, where R is H, D, C1-20 alkyl, or fluoroalkyl.

The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms joined by a bond).

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. An alternative embodiment of the disclosed subject matter hereof, is described as consisting essentially of certain features or elements, in which embodiment features or elements that would materially after the principle of operation or the distinguishing characteristics of the embodiment are not present therein. A further alternative embodiment of the described subject matter hereof is described as consisting of certain features or elements, in which embodiment, or in insubstantial variations thereof, only the features or elements specifically stated or described are present.

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics,* 81$^{st}$ Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

To the extent not described herein, many details regarding specific materials, processing acts, and circuits are conventional and may be found in textbooks and other sources within the organic light-emitting diode display, photodetector, photovoltaic, and semiconductive member arts.

2. ELECTROACTIVE COMPOUND

The compound described herein has Formula I

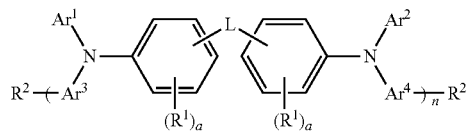

Formula I wherein:
Ar$^1$ through Ar$^4$ are the same or different and are aryl groups;
L is selected from the group consisting of a spiro group, an adamantyl group, bicyclic cyclohexyl, deuterated analogs thereof, and substituted derivatives thereof;
R$^1$ is the same or different at each occurrence and is selected from the group consisting of D, F, alkyl, aryl, alkoxy, silyl, and a crosslinkable group, where adjacent R$^1$ groups can be joined together to form an aromatic ring;
R$^2$ is the same or different at each occurrence and is selected from the group consisting of H, D, and halogen;
a is the same or different at each occurrence and is an integer from 0-4; and
n is an integer greater than 0.

The compound having Formula I can be a small molecule with n=1, an oligomer, or a polymer. In some embodiments, the compound is a polymer with $M_n > 20,000$; in some embodiments, $M_n > 50,000$.

In some embodiments of Formula I, n=1 and R$^2$ is halogen. Such compounds can be useful as monomers for the formation of polymeric compounds. In some embodiments, the halogen is Cl or Br; in some embodiments, Br.

In some embodiments of Formula I, n=1 and R$^2$ is H or D.

In some embodiments, the compound having Formula I is deuterated. The term "deuterated" is intended to mean that at least one H has been replaced by D. The term "deuterated analog" refers to a structural analog of a compound or group in which one or more available hydrogens have been replaced with deuterium. In a deuterated compound or deuterated analog, the deuterium is present in at least 100 times the natural abundance level. In some embodiments, the compound is at least 10% deuterated. By "% deuterated" or "% deuteration" is meant the ratio of deuterons to the sum of protons plus deuterons, expressed as a percentage. In some embodiments, the compound is at least 10% deuterated; in some embodiments, at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

Deuterated materials can be less susceptible to degradation by holes, electrons, excitons, or a combination thereof. Deuteration can potentially inhibit degradation of the compound during device operation, which in turn can lead to improved device lifetime. In general, this improvement is accomplished without sacrificing other device properties. Furthermore, the deuterated compounds frequently have greater air tolerance than the non-deuterated analogs. This can result in greater processing tolerance both for the preparation and purification of the materials and in the formation of electronic devices using the materials.

In Formula I, the L linking group provides a break in conjugation between two arylamino groups. In some embodiments, the L group provides a degree of linearity such that the angle α, shown below, is greater than the tetrahedral angle of 109.5°.

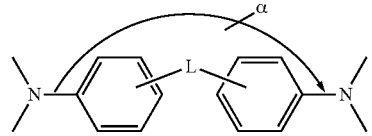

In some embodiments, α is greater than 120°; in some embodiments, greater than 140°; in some embodiments, greater than 160°.

A Spiro group is a bicyclic organic compound with rings connected through a single atom. The rings can be different in nature or identical. The connecting atom is called the spiroatom. In some embodiments, the spiroatom is selected from the group consisting of C and Si.

In some embodiments of Formula I, the compounds have L with one of the core structures given below

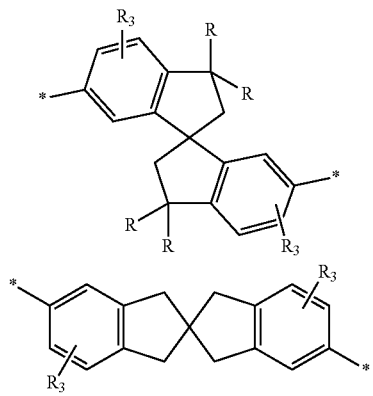

-continued

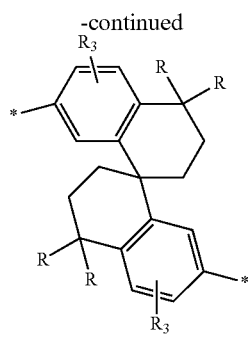

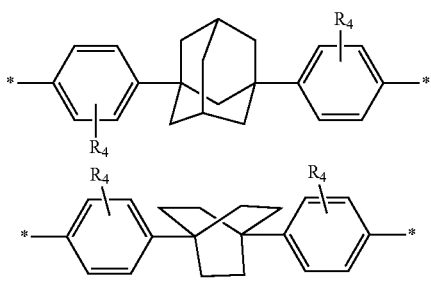

where the asterisk indicates the point of attachment to the nitrogen of the arylamino group and R is the same or different at each occurrence and is H or $R^1$.

In some embodiments of Formula I, $Ar^1$ and $Ar^2$ are aryl groups having no fused rings. In some embodiments, $Ar^1$ and $Ar^2$ have Formula a

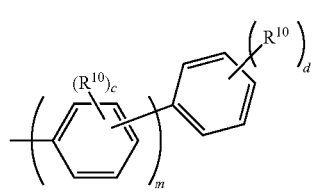

Formula a where:
$R^{10}$ is the same or different at each occurrence and is selected from the group consisting of D, alkyl, alkoxy, siloxane and silyl;
c is the same or different at each occurrence and is an integer from 0-4;
d is an integer from 0-5; and
m is an integer from 1 to 5.

In some embodiments, $Ar^1$ and $Ar^2$ have Formula b

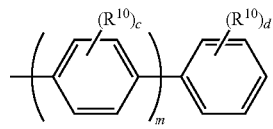

Formula b where:
$R^{10}$ is the same or different at each occurrence and is selected from the group consisting of D, alkyl, alkoxy, siloxane and silyl;
c is the same or different at each occurrence and is an integer from 0-4;
d is an integer from 0-5; and
m is an integer from 1 to 5.

In some embodiments of Formulae a and b, at east one of c and d is not zero. In some embodiments, m=1-3.

In some embodiments of Formula I, $Ar^1$ and $Ar^2$ are selected from the group consisting of phenyl, biphenyl, terphenyl, deuterated derivatives thereof, and derivatives thereof having one or more substituents selected from the group consisting of alkyl, alkoxy, silyl, and a substituent with a crosslinking group.

In some embodiments of Formula I, a=0.

In some embodiments of Formula I, $R^1$ is D or $C_{1-10}$ alkyl. In some embodiments, the alkyl group is deuterated. In some embodiments, a=4 and $R^1$=D.

In some embodiments of Formula I, there can be any combination of the following: (i) deuteration; (ii) the angle α is greater than 109.5°; (iii) L is selected from the group

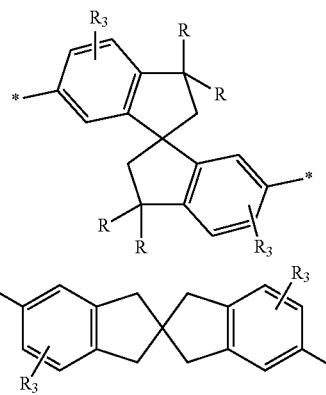

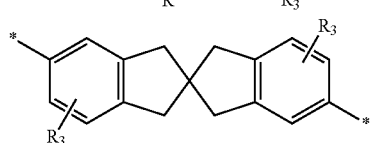

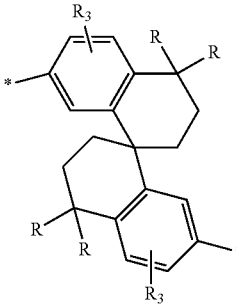

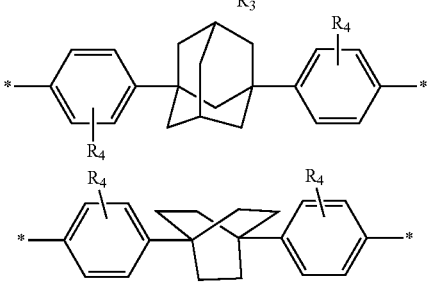

as defined above; (iv) $Ar^1$ and $Ar^2$ are selected from the group consisting of phenyl, biphenyl, terphenyl, deuterated derivatives thereof, derivatives thereof having one or more substituents selected from the group consisting of alkyl, alkoxy, silyl, and a substituent with a crosslinking group, a group having Formula a, and a group having Formula b; (v) a=0 or a is not 0 and $R^1$ is D, $C_{1-10}$ alkyl, or deuterated $C_{1-10}$ alkyl.

In some embodiments, the compound having Formula I is further defined by Formula II

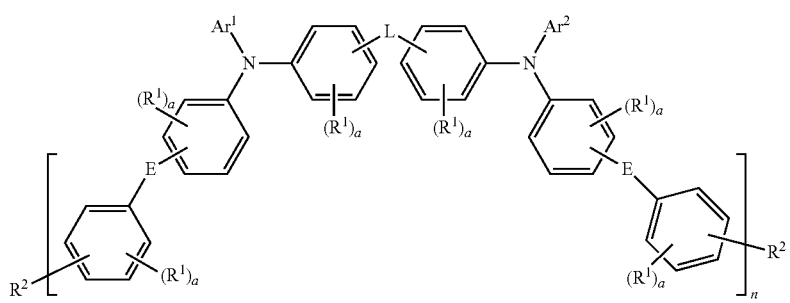

wherein:
- $Ar^1$ and $Ar^2$ are the same or different and are aryl groups;
- L is selected from the group consisting of a spiro group, an adamantyl group, bicyclic cyclohexyl, deuterated analogs thereof, and substituted derivatives thereof;
- E is the same or different at each occurrence and is selected from the group consisting of a single bond, $C(R^3)_2$, $C(R^4)_2C(R^4)_2$, O, $Si(R^3)_2$, $Ge(R^3)_2$;
- $R^1$ is the same or different at each occurrence and is selected from the group consisting of D, F, alkyl, alyl, alkoxy, silyl, and a crosslinkable group, where adjacent $R^1$ groups can be joined together to form an aromatic ring;
- $R^2$ is the same or different at each occurrence and is selected from the group consisting of H, D, and halogen;
- $R^3$ is the same or different at each occurrence and is selected from the group consisting of alkyl and aryl, where adjacent $R^3$ groups can be joined together to form an aliphatic ring;
- $R^4$ is the same or different at each occurrence and is selected from the group consisting of H, D, and alkyl;
- a is the same or different at each occurrence and is an integer from 0-4; and
- n is an integer greater than 0.

The compound having Formula II can be a small molecule with n=1, an oligomer, or a polymer. In some embodiments, the compound is a polymer with $M_n$>20,000; in some embodiments, $M_n$>50,000.

In some embodiments of Formula II, n=1 and $R^2$ is halogen. Such compounds can be useful as monomers for the formation of polymeric compounds. In some embodiments, the halogen is Cl or Br; in some embodiments, Br.

In some embodiments of Formula II, n=1 and $R^2$ is H or D.

In some embodiments, the compound having Formula II is deuterated.

In some embodiments of Formula II, L is selected from the groups shown below

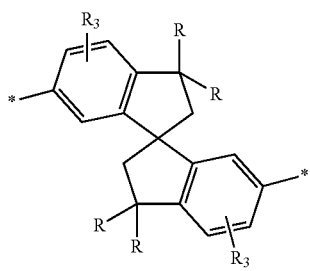

-continued

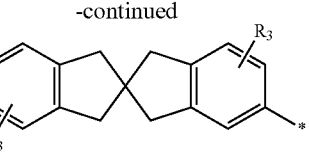

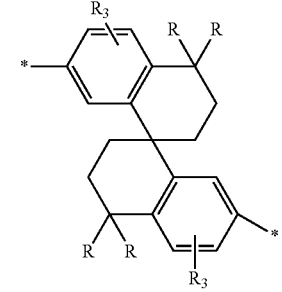

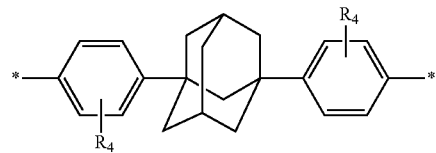

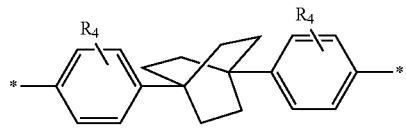

where the asterisk indicates the point of attachment to the nitrogen of the arylamino group and R is the same or different at each occurrence and is H or $R^1$.

In some embodiments of Formula II, $Ar^1$ and $Ar^2$ are aryl groups having no fused rings. In some embodiments, $Ar^1$ and $Ar^2$ have Formula a or Formula b, as defined above. In some embodiments of Formulae a and b, at least one of c and d is not zero. In some embodiments, m=1-3.

In some embodiments of Formula II, $Ar^1$ and $Ar^2$ are selected from the group consisting of phenyl, biphenyl, terphenyl, deuterated derivatives thereof, and derivatives thereof having one or more substituents selected from the group consisting of alkyl, alkoxy, silyl, and a substituent with a crosslinking group.

In some embodiments of Formula I, a=0.

In some embodiments of Formula I, $R^1$ is D or $C_{1-10}$ alkyl. In some embodiments, the alkyl group is deuterated. In some embodiments, a=4 and $R^1$=D.

In some embodiments of Formula II, E is selected from the group consisting of $C(R^3)_2$ and $C(R^4)_2C(R^4)_2$. In some embodiments, $R^3$ is selected from the group consisting of phenyl, biphenyl, and fluoroalkyl. In some embodiments, $R^4$ is selected from the group consisting of H and D.

In some embodiments of Formula II, there can be any combination of the following: (i) deuteration; (ii) the angle α is greater than 109.5°; (iii) L is selected from the group

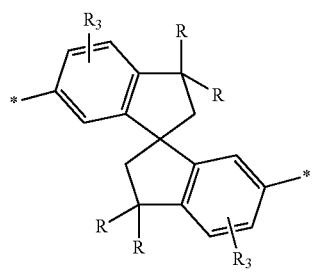

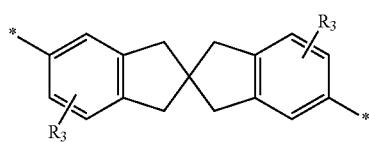

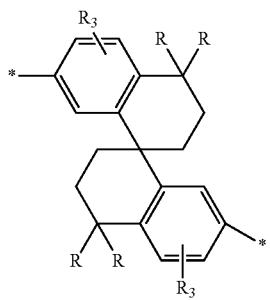

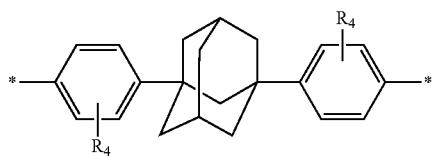

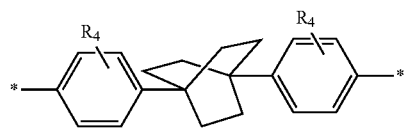

as defined above; (iv) $Ar^1$ and $Ar^2$ are selected from the group consisting of phenyl, biphenyl, terphenyl, deuterated derivatives thereof, derivatives thereof having one or more substituents selected from the group consisting of alkyl, alkoxy, silyl, and a substituent with a crosslinking group, a group having Formula a, and a group having Formula b; (v) a=0, or a is not 0 and $R^1$ is D, $C_{1-10}$ alkyl, or deuterated $C_{1-10}$ alkyl; (vi) E is selected from the group consisting of $C(R^3)_2$ and $C(R^4)_2C(R^4)_2$; (vii) $R^3$ is selected from the group consisting of phenyl, biphenyl, and fluoroalkyl; (viii) $R^4$ is selected from the group consisting of H and D. In some embodiments, the compound having Formula I is further defined by Formula III Formula III

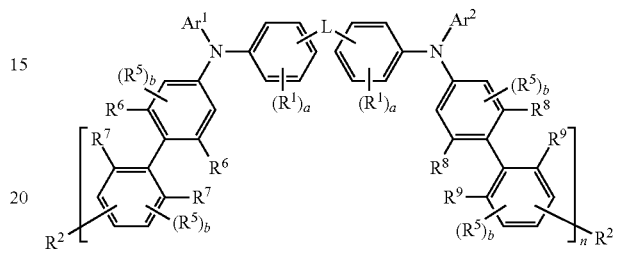

wherein:
$Ar^1$ and $Ar^2$ are the same or different and are aryl groups;

L is selected from the group consisting of a spiro group, an adamantyl group, bicyclic cyclohexyl, deuterated analogs thereof, and substituted derivatives thereof;

$R^1$ is the same or different at each occurrence and is selected from the group consisting of D, F, alkyl, aryl, alkoxy, silyl, and a crosslinkable group, where adjacent $R^1$ groups can be joined together to form an aromatic ring;

$R^2$ is the same or different at each occurrence and is selected from the group consisting of H, D, and halogen;

$R^5$ is the same or different at each occurrence and is selected from the group consisting of D, F, alkyl, aryl, alkoxy, silyl, and a crosslinkable group;

$R^6$ through $R^9$ are the same or different at each occurrence and are selected from the group consisting of H, D, F, alkyl, aryl, alkoxy, silyl, and a crosslinkable group, with the proviso that at least one of $R^6$ and $R^7$ is alkyl or silyl, and at least one of $R^8$ and $R^9$ is alkyl or silyl;

a is the same or different at each occurrence and is an integer from 0-4;

b is the same or different at each occurrence and is an integer from 0-2; and n is an integer greater than 0.

The compound having Formula III can be a small molecule with n=1, an oligomer, or a polymer. In some embodiments, the compound is a polymer with $M_n$>20,000; in some embodiments, $M_n$>50,000.

In some embodiments of Formula III, n=1 and $R^2$ is halogen. Such compounds can be useful as monomers for the formation of polymeric compounds. In some embodiments, the halogen is Cl or Br; in some embodiments, Br.

In some embodiments of Formula III, n=1 and $R^2$ is H or D.

In some embodiments, the compound having Formula III is deuterated.

In some embodiments of Formula III, L is selected from the groups shown below

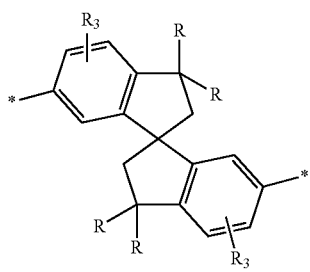

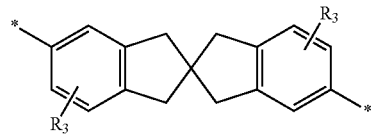

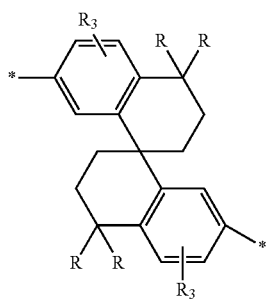

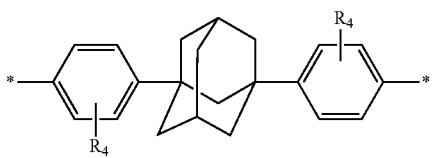

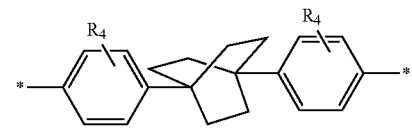

where the asterisk indicates the point of attachment to the nitrogen of the arylamino group and R is the same or different at each occurrence and is H or $R^1$.

In some embodiments of Formula III, $Ar^1$ and $Ar^2$ are aryl groups having no fused rings. In some embodiments, $Ar^1$ and $Ar^2$ have Formula a or Formula b, as defined above. In some embodiments of Formulae a and b, at least one of c and d is not zero. In some embodiments, m=1-3.

In some embodiments of Formula III, $Ar^1$ and $Ar^2$ are selected from the group consisting of phenyl, biphenyl, terphenyl, deuterated derivatives thereof, and derivatives thereof having one or more substituents selected from the group consisting of alkyl, alkoxy, silyl, and a substituent with a crosslinking group.

In some embodiments of Formula III, all a=0.

In some embodiments of Formula III, a is not 0 and $R^1$ is D or $C_{1-10}$ alkyl. In some embodiments, the alkyl group is deuterated. In some embodiments, all a=4 and $R^1$=D.

In some embodiments of Formula III, all b=0.

In some embodiments of Formula III, b is not 0 and $R^2$ is D or $C_{1-10}$ alkyl. In some embodiments, the alkyl group is deuterated. In some embodiments, all h=2 and $R^2$=D.

In some embodiments of Formula III, $R^6$=$R^8$=alkyl or deuterated alkyl. In some embodiments, $R^7$=$R^9$=alkyl or deuterated alkyl.

In some embodiments of Formula III, there can be any combination of the following: (i) deuteration; (ii) the angle α is greater than 109.5°; (iii) L is selected from the group

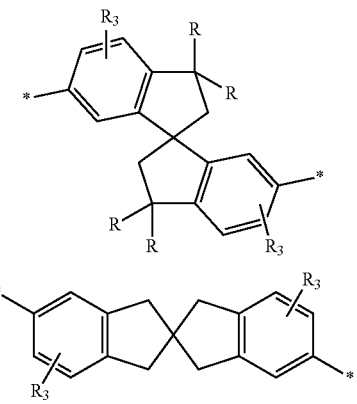

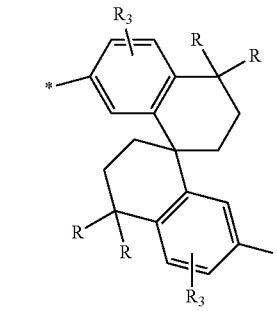

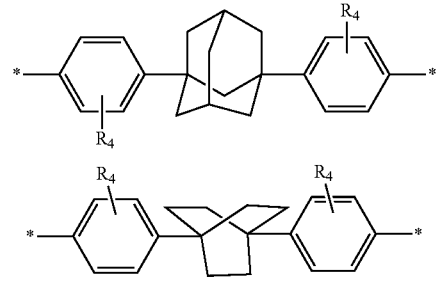

as defined above; (iv) $Ar^1$ and $Ar^2$ are selected from the group consisting of phenyl, biphenyl, terphenyl, deuterated derivatives thereof, derivatives thereof having one or more substituents selected from the group consisting of alkyl, alkoxy, silyl, and a substituent with a crosslinking group, a group having Formula a, and a group having Formula b; (v) a=0, or a is not 0 and $R^1$ is D, $C_{1-10}$ alkyl, or deuterated $C_{1-10}$ alkyl; (vi) b=0, or b is not 0 and $R^2$ is D, $C_{1-10}$ alkyl, or deuterated $C_{1-10}$ alkyl; (vii) $R^6$=$R^8$=alkyl or deuterated alkyl; (viii) $R^7$=$R^9$=alkyl or deuterated alkyl.

Some non-limiting examples of compounds having Formula I are shown below.

Compound A
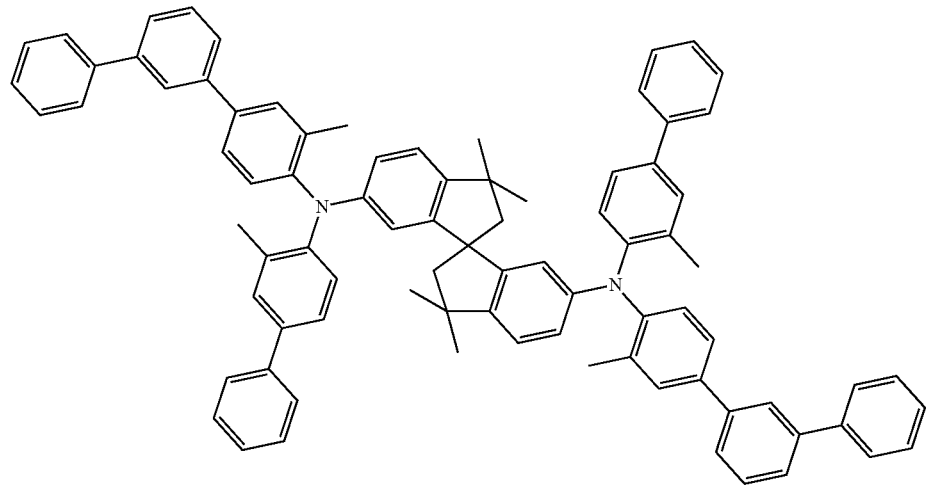
Compound B
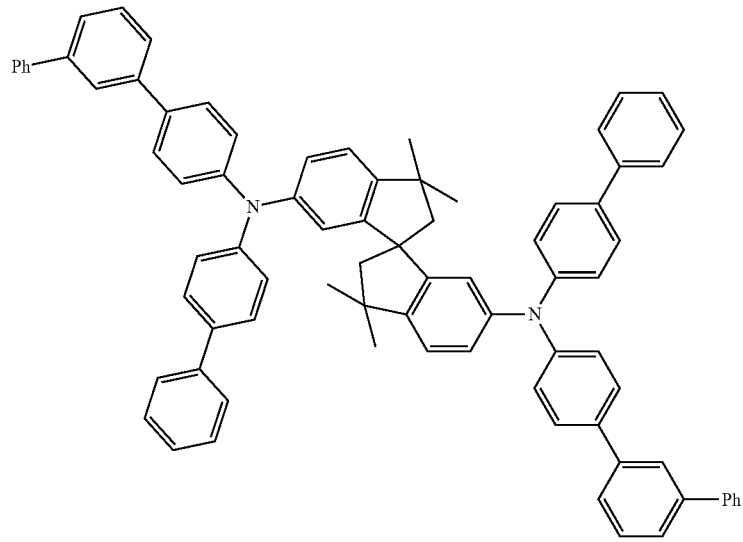
Compound C
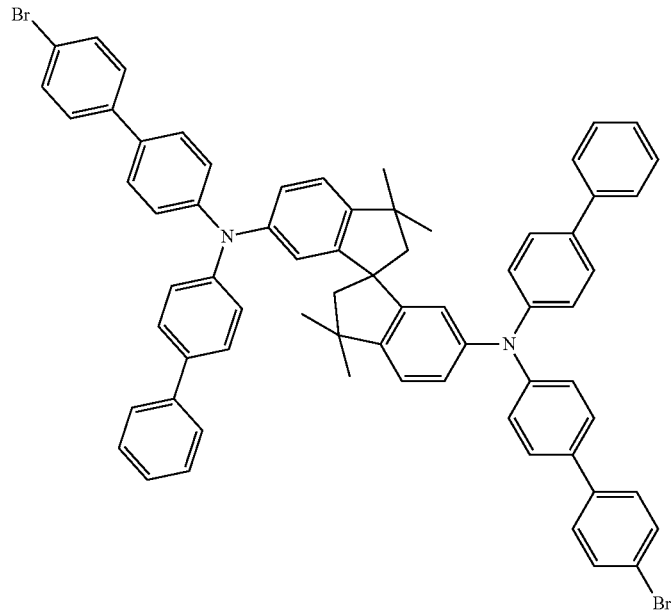

-continued

Compound D

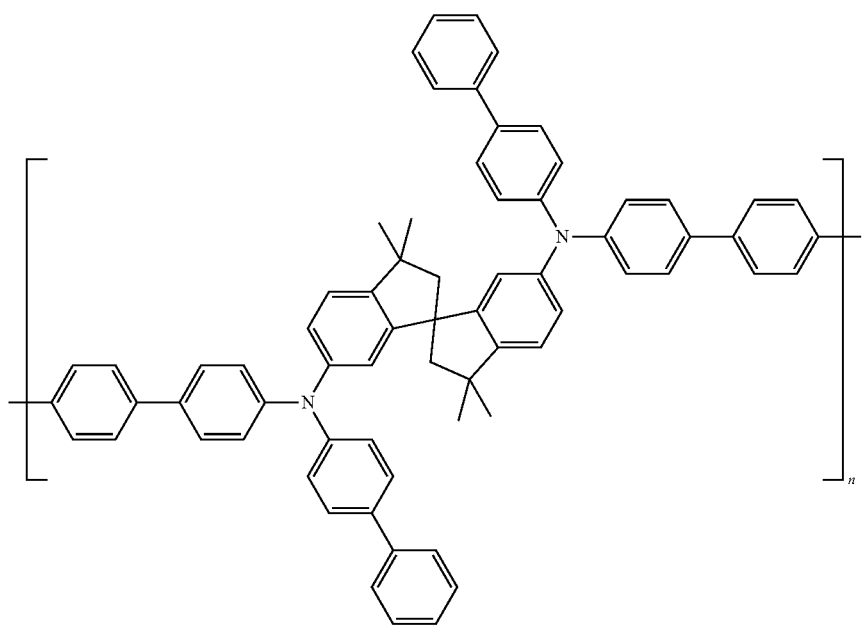

The new compounds can be made using any technique that will yield a C—C or C—N bond. A variety of such techniques are known, such as Suzuki, Yamamoto, Stille, and Pd- or Ni-catalyzed C—N couplings. Deuterated compounds can be prepared in a similar manner using deuterated precursor materials or, more generally, by treating the non-deuterated compound with deuterated solvent, such as d6-benzene, in the presence of a Lewis acid H/D exchange catalyst, such as aluminum trichloride or ethyl aluminum dichloride. Exemplary preparations are given in the Examples.

The compounds can be formed into layers using solution processing techniques. The term "layer" is used interchangeably with the term "film" and refers to a coating covering a desired area. The term is not limited by size. The area can be as large as an entire device or as small as a specific functional area such as the actual visual display, or as small as a single sub-pixel. Layers and films can be formed by any conventional deposition technique, including vapor deposition, liquid deposition (continuous and discontinuous techniques), and thermal transfer. Continuous deposition techniques, include but are not limited to, spin coating, gravure coating, curtain coating, dip coating, slot-die coating, spray coating, and continuous nozzle coating. Discontinuous deposition techniques include, but are not limited to, ink jet printing, gravure printing, and screen printing.

The new compounds described herein have can be used as hole transport materials, as electroactive materials, and as hosts for electroluminescent materials. The new compounds also have utility as materials for a priming layer to improve the deposition of a hole transport layer.

The new compounds have hole mobilities and HOMO/LUMO energies similar to efficient small molecule hole transport compounds such as N,N'-diphenyl-N,N'-bis(3-methylphenyl)-[1,1'-biphenyl]-4,4'-diamine (TPD). Compounds such as TPD generally must be applied using a vapor deposition technique.

3. ELECTRONIC DEVICES

Organic electronic devices that may benefit from having one or more layers comprising at least one compound as described herein include, but are not limited to, (1) devices that convert electrical energy into radiation (e.g., a light-emitting diode, light emitting diode display, lighting device, luminaire, or diode laser), (2) devices that detect signals through electronics processes (e.g., photodetectors, photoconductive cells, photoresistors, photoswitches, phototransistors, phototubes, IR detectors, biosensors), (3) devices that convert radiation into electrical energy, (e.g., a photovoltaic device or solar cell), and (4) devices that include one or more electronic components that include one or more organic semi-conductor layers (e.g., a transistor or diode). Other uses for the compositions according to the present invention include coating materials for memory storage devices, antistatic films, biosensors, electrochromic devices, solid electrolyte capacitors, energy storage devices such as a rechargeable battery, and electromagnetic shielding applications.

One illustration of an organic electronic device structure is shown in FIG. 1. The device 100 has a first electrical contact layer, an anode layer 110 and a second electrical contact layer, a cathode layer 160, and an electroactive layer 140 between them. Additional layers may optionally be present. Adjacent to the anode may be a hole injection layer 120, sometimes referred to as a buffer layer. Adjacent to the hole injection layer may be a hole transport layer 130, comprising hole transport material. Adjacent to the cathode may be an electron transport layer 150, comprising an electron transport material. As an option, devices may use one or more additional hole injection or hole transport layers (not shown) next to the anode 110 and/or one or more additional electron injection or electron transport layers (not shown) next to the cathode 160. Layers 120 through 150 are individually and collectively referred to as the electroactive layers.

Figure 2:
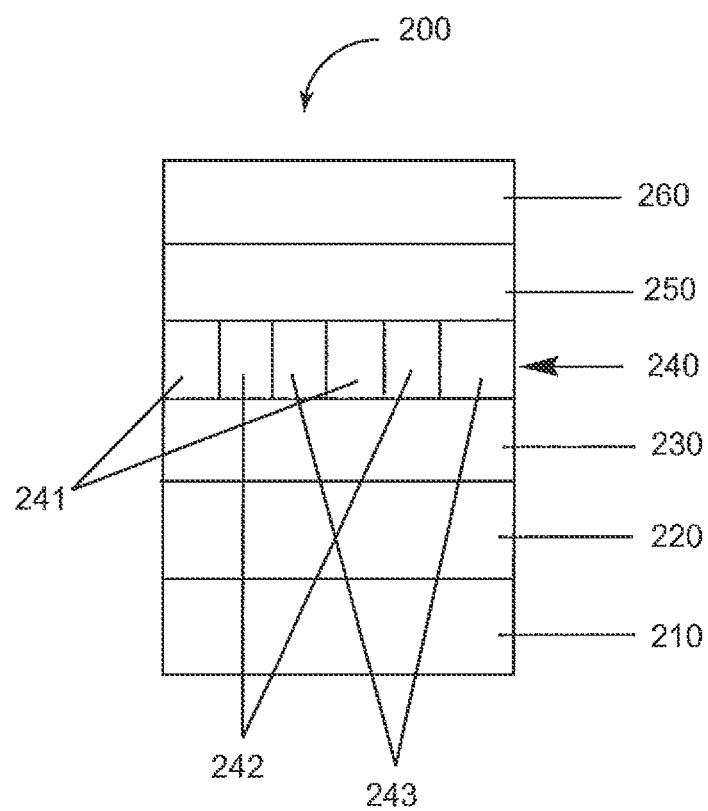
FIG. 2 includes an illustration of another example of an organic electronic device.

In some embodiments, in order to achieve full color, the light-emitting layer is pixellated, with subpixel units for each of the different colors. An illustration of a pixellated device is shown in FIG. 2. The device 200 has anode 210, hole injection layer 220, hole transport layer 230, electroluminescent layer 240, electron transport layer 250, and cathode 260. The electroluminescent layer is divided into subpixels 241, 242, 243, which are repeated across the layer. In some embodiments, the subpixels represent red, blue and green color emission. Although three different subpixel units are depicted in FIG. 2, two or more than three subpixel units may be used.

The different layers will be discussed further herein with reference to FIG. 1. However, the discussion applies to FIG. 2 and other configurations as well.

In one embodiment, the different layers have the following range of thicknesses: anode 110, 500-5000 Å, in one embodiment 1000-2000 Å; hole injection layer 120, 50-2000 Å, in one embodiment 200-1000 Å; hole transport layer 130, 50-2000 Å, in one embodiment 200-1000 Å; electroactive layer 140, 10-2000 Å, in one embodiment 100-1000 Å; electron transport layer 150, 50-2000 Å, in one embodiment 100-1000 Å; cathode 160, 200-10000 Å, in one embodiment 300-5000 Å. The desired ratio of layer thicknesses will depend on the exact nature of the materials used.

One or more of the new compounds having Formula I described herein may be present in one or more of the electroactive layers of a device. In some embodiments, the new compounds are useful as hole transport materials in layer 130. In some embodiments, the new compounds are useful as host materials for electroactive dopant materials in electroactive layer 140. The term "dopant" is intended to mean a material, within a layer including a host material, that changes the electronic characteristic(s) or the targeted wavelength(s) of radiation emission, reception, or filtering of the layer compared to the electronic characteristic(s) or the wavelength(s) of radiation emission, reception, or filtering of the layer in the absence of such material. The term "host material" is intended to mean a material to which a dopant is added. The host material may or may not have electronic characteristic(s) or the ability to emit, receive, or filter radiation. In some embodiments, the host material is present in higher concentration.

The anode 110 is an electrode that is particularly efficient for injecting positive charge carriers. It can be made of, for example materials containing a metal, mixed metal, alloy, metal oxide or mixed-metal oxide, or it can be a conducting polymer, and mixtures thereof. Suitable metals include the Group 11 metals, the metals in Groups 4, 5, and 6, and the Group 8-10 transition metals. If the anode is to be light-transmitting, mixed-metal oxides of Groups 12, 13 and 14 metals, such as indium-tin-oxide, are generally used. The anode may also comprise an organic material such as polyaniline as described in "Flexible light-emitting diodes made from soluble conducting polymer," Nature vol. 357, pp 477 479 (11 Jun. 1992). At least one of the anode and cathode should be at least partially transparent to allow the generated light to be observed.

Optional hole injection layer 120 comprises hole injection materials. The term "hole injection layer" or "hole injection material" is intended to mean electrically conductive or semiconductive materials and may have one or more functions in an organic electronic device, including but not limited to, planarization of the underlying layer, charge transport and/or charge injection properties, scavenging of impurities such as oxygen or metal ions, and other aspects to facilitate or to improve the performance of the organic electronic device. Hole injection materials may be polymers, oligomers, or small molecules, and may be in the form of solutions, dispersions, suspensions, emulsions, colloidal mixtures, or other compositions.

The hole injection layer can be formed with polymeric materials, such as polyaniline (PAM) OF polyethylenedi- oxythiophene (PEDOT), which are often doped with protonic adds. The protonic adds can be, for example, poly (styrenesulfonic add), poly(2-acrylaoido-2-methyl-1-propanesulfonic add), and the like. The hole injection layer 120 can comprise charge transfer compounds, and the like, such as copper phthalocyanine and the tetrathiafulvalene-tetracyanoquinodimethane system (TTF-TCNQ). In one embodiment, the hole injection layer 120 is made from a dispersion of a conducting polymer and a colloid-forming polymeric acid. Such materials have been described in, for example, published U.S. patent applications 2004-0102577, 2004-0127637, and 2005-0205860.

Layer 130 comprises hole transport material. In some embodiments, the hole transport layer comprises a compound having Formula I. In some embodiments, the hole transport layer consists essentially of a compound having Formula I.

In some embodiments, layer 130 comprises other hole transport material. Examples of hole transport materials for the hole transport layer have been summarized for example, in Kirk-Othmer Encyclopedia of Chemical Technology, Fourth Edition, Vol. 18, p. 837-860, 1996, by Y. Wang. Both hole transporting small molecules and polymers can be used. Commonly used hole transporting molecules include, but are not limited to: 4,4',4"-tris(N,N-diphenyl-amino)-triphenylamine (TDATA); 4,4',4"-tris(N-3-methylphenyl-N-phenyl-amino)-triphenylamine (MTDATA); N,N'-diphenyl-N,N'-bis(3-methylphenyl)-[1,1'-biphenyl]-4,4'-diamine (TPD); 4,4'-bis(carbazol-9-yl)biphenyl (CBP); 1,3-bis(carbazol-9-yl)benzene (mCP); 1,1-bis[(di-4-tolylamino) phenyl]cyclohexane (TAPC); N,N'-bis(4-methylphenyl)-N,N'-bis(4-ethylphenyl)-[1,1'-(3,3'-dimethyl)biphenyl]-4,4'-diamine (ETPD); tetrakis-(3-methylphenyl)-N,N,N',N'-2,5-phenylenediamine (PDA); α-phenyl-4-N,N-diphenylaminostyrene (TPS); p-(diethylamino) benzaldehyde diphenylhydrazone (DEH); triphenylamine (TPA); bis[4-(N,N-diethylamino)-2-methylphenyl](4-methylphenyl)methane (MPMP); 1-phenyl-3-[p-(diethylamino) styryl]-5-[p-(diethylamino)phenyl]pyrazoline (PPR OF DEASP); 1,2-trans-bis(9H-carbazol-9-yl)cyclobutane (DCZB); N,N,N',N'-tetrakis(4-methylphenyl)-(1,1-biphenyl)-4,4'-diamine (TTB); N,N'-bis(naphthalen-1-yl)-N,N'-bis-(phenyl)benzidine (α-NPB); and porphyrinic compounds, such as copper phthalocyanine. Commonly used hole transporting polymers include, but are not limited to, polyvinylcarbazole, (phenylmethyl)polysilane, poly(dioxythiophenes), polyanilines, and polypyrroles. It is also possible to obtain hole transporting polymers by doping hole transporting molecules such as those mentioned above into polymers such as polystyrene and polycarbonate. In some cases, triarylamine polymers are used, especially triarylamine-fluorene copolymers. In some cases, the polymers and copolymers are crosslinkable. Examples of crosslinkable hole transport polymers can be found in, for example, published US patent application 2005-0184287 and published POT application WO 2005/052027. In some embodiments, the hole transport layer is doped with a p-dopant, such as tetrafluorotetracyanoquinodimethane and perylene-3,4,9,10-tetracarboxylic-3,4,9,10-dianhydride.

Depending upon the application of the device, the electroactive layer 140 can be a light-emitting layer that is activated by an applied voltage (such as in a light-emitting diode or light-emitting electrochemical cell), a layer of material that responds to radiant energy and generates a signal with or without an applied bias voltage (such as in a photodetector). In one embodiment, the electroactive layer comprises an organic electroluminescent ("EL") material.

Any EL material can be used in the devices, including, but not limited to, small molecule organic fluorescent compounds, fluorescent and phosphorescent metal complexes, conjugated polymers, and mixtures thereof. Examples of fluorescent compounds include, but are not limited to, chrysenes, pyrenes, perylenes, rubrenes, coumarins, anthracenes, thiadiazoles, derivatives thereof, and mixtures thereof. Examples of metal complexes include, but are not limited to, metal chelated oxinoid compounds, such as tris(8-hydroxyquinolato)aluminum (Alq3); cyclometalated iridium and platinum electroluminescent compounds, such as complexes of iridium with phenylpyridine, phenylquinoline, or phenylpyrimidine ligands as disclosed in Petrov et al., U.S. Pat. No. 6,670,645 and Published POT Applications WO 03/063555 and WO 2004/016710, and organometallic complexes described in, for example, Published POT Applications WO 03/008424, WO 03/091688, and WO 03/040257, and mixtures thereof. In some cases the small molecule fluorescent or organometallic materials are deposited as a dopant with a host material to improve processing and/or electronic properties. Examples of conjugated polymers include, but are not limited to poly(phenylenevinylenes), polyfluorenes, poly(spirobifluorenes), polythiophenes, poly(p-phenylenes), copolymers thereof, and mixtures thereof.

In some embodiments, electroactive layer 140 comprises an electroluminescent material in a host material having Formula I. In some embodiments, a second host material is also present. In some embodiments, electroactive layer 140 consists essentially of an electroluminescent material and a host material having Formula I. In some embodiment, electroactive layer 140 consists essentially of an electroluminescent material, a first host material having Formula I, and a second host material. Examples of second host materials include, but are not limited to, chrysenes, phenanthrenes, triphenylenes, phenanthrolines, naphthalenes, anthracenes, quinolines, isoquinolines, quinoxalines, phenylpyridines, benzodifurans, and metal quinolinate complexes.

Optional layer 150 can function both to facilitate electron transport, and also serve as a hole injection layer or confinement layer to prevent quenching of the exciton at layer interfaces. Preferably, this layer promotes electron mobility and reduces exciton quenching. Examples of electron transport materials which can be used in the optional electron transport layer 150, include metal chelated oxinoid compounds, including metal quinolate derivatives such as tris(8-hydroxyquinolato)aluminum (AlQ), bis(2-methyl-8-quinolinolato)(p-phenylphenolato) aluminum (BAlq), tetrakis-(8-hydroxyquinolato)hafnium (HfQ) and tetrakis-(8-hydroxyquinolato)zirconium (ZrQ); and azole compounds such as 2-(4-biphenylyl)-5-(4-t-butylphenyl)-1,3,4-axadiazole (PBD), 3-(4-biphenylyl)-4-phenyl-5-(4-t-butylphenyl)-1,2,4-triazole (TAZ), and 1,3,5-tri(phenyl-2-benzimidazole) benzene (TPBI); quinoxaline derivatives such as 2,3-bis(4-fluorophenyl)quinoxaline; phenanthrolines such as 4,7-diphenyl-1,10-phenanthroline (DPA) and 2,9-dimethyl-4,7-diphenyl-1,10-phenanthroline (DDPA); triazines; fullerenes; and mixtures thereof. In some embodiments, the electron transport material is selected from the group consisting of metal quinolates and phenanthroline derivatives. In some embodiments, the electron transport layer further comprises an n-dopant. N-dopant materials are well known. The n-dopants include, but are not limited to, Group 1 and 2 metals; Group 1 and 2 metal salts, such as LiF, CsF, and $Cs_2CO_3$; Group 1 and 2 metal organic compounds, such as Li quinolate; and molecular n-dopants, such as leuco dyes, metal complexes, such as $W_2(hpp)_4$ where hpp=1,3,4,6,7,8-hexahydro-2H-pyrimido-[1,2-a]-pyrimidine and cobaltocene, tetrathianaphthacene, bis(ethylenedithio)tetrathiafulvalene, heterocyclic radicals or diradicals, and the dimers, oligomers, polymers, dispiro compounds and polycycles of heterocyclic radical or diradicals.

The cathode 160, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li-containing organometallic compounds, LiF, $Li_2O$, Cs-containing organometallic compounds, CsF, $Cs_2O$, and $Cs_2CO_3$ can also be deposited between the organic layer and the cathode layer to lower the operating voltage. This layer may be referred to as an electron injection layer. When an electron injection layer is present, the amount of material deposited is generally in the range of 1-100 Å, in one embodiment 1-10 Å.

It is known to have other layers in organic electronic devices. For example, there can be a layer (not shown) between the anode 110 and hole injection layer 120 to control the amount of positive charge injected and/or to provide band-gap matching of the layers, or to function as a protective layer. Layers that are known in the art can be used, such as copper phthalocyanine, silicon oxy-nitride, fluorocarbons, silanes, or an ultra-thin layer of a metal, such as Pt. Alternatively, some or all of anode layer 110, electroactive layers 120, 130, 140, and 150, or cathode layer 160, can be surface-treated to increase charge carrier transport efficiency. The choice of materials for each of the component layers is preferably determined by balancing the positive and negative charges in the emitter layer to provide a device with high electroluminescence efficiency.

It is understood that each functional layer can be made up of more than one layer.

The device layers can be formed by any deposition technique, or combinations of techniques, including vapor deposition, liquid deposition, and thermal transfer. Substrates such as glass, plastics, and metals can be used. Conventional vapor deposition techniques can be used, such as thermal evaporation, chemical vapor deposition, and the like. The organic layers can be applied from solutions or dispersions in suitable solvents, using conventional coating or printing techniques, including but not limited to spin-coating, dip-coating, roll-to-roll techniques, ink-jet printing, continuous nozzle printing, screen-printing, gravure printing and the like.

For liquid deposition methods, a suitable solvent for a particular compound or related class of compounds can be readily determined by one skilled in the art. For some applications, it is desirable that the compounds be dissolved in non-aqueous solvents. Such non-aqueous solvents can be relatively polar, such as $C_1$ to $C_{20}$ alcohols, ethers, and acid esters, or can be relatively non-polar such as $C_1$ to $C_{12}$ alkanes or aromatics such as toluene, xylenes, trifluorotoluene and the like. Other suitable liquids for use in making the liquid composition, either as a solution or dispersion as described herein, comprising the new compounds, includes, but not limited to, chlorinated hydrocarbons (such as methylene chloride, chloroform, chlorobenzene), aromatic hydrocarbons (such as substituted and non-substituted toluenes and xylenes), including triflurotoluene), polar solvents (such as tetrahydrofuran (THP), N-methyl pyrrolidone) esters (such as ethylacetate) alcohols (isopropanol), keytones (cyclopentatone) and mixtures thereof. Suitable solvents for electroluminescent materials have been described in, for example, published POT application WO 2007/1145979.

In some embodiments, the device is fabricated by liquid deposition of the hole injection layer, the hole transport layer, and the electroactive layer, and by vapor deposition of the anode, the electron transport layer, an electron injection layer and the cathode.

It is understood that the efficiency of devices made with the new compositions described herein, can be further improved by optimizing the other layers in the device. For example, more efficient cathodes such as Ca, Ba or LiF can be used. Shaped substrates and novel hole transport materials that result in a reduction in operating voltage or increase quantum efficiency are also applicable. Additional layers can also be added to tailor the energy levels of the various layers and facilitate electroluminescence.

In one embodiment, the device has the following structure, in order: anode, hole injection layer, hole transport layer, electroactive layer, electron transport layer, electron injection layer, cathode.

Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety.

EXAMPLES

The concepts described herein will be further described in the following examples, which do not limit the scope of the invention described in the claims.

Example 1

This example illustrates the preparation of Compounds C and D.

The compounds were prepared according to the following scheme:

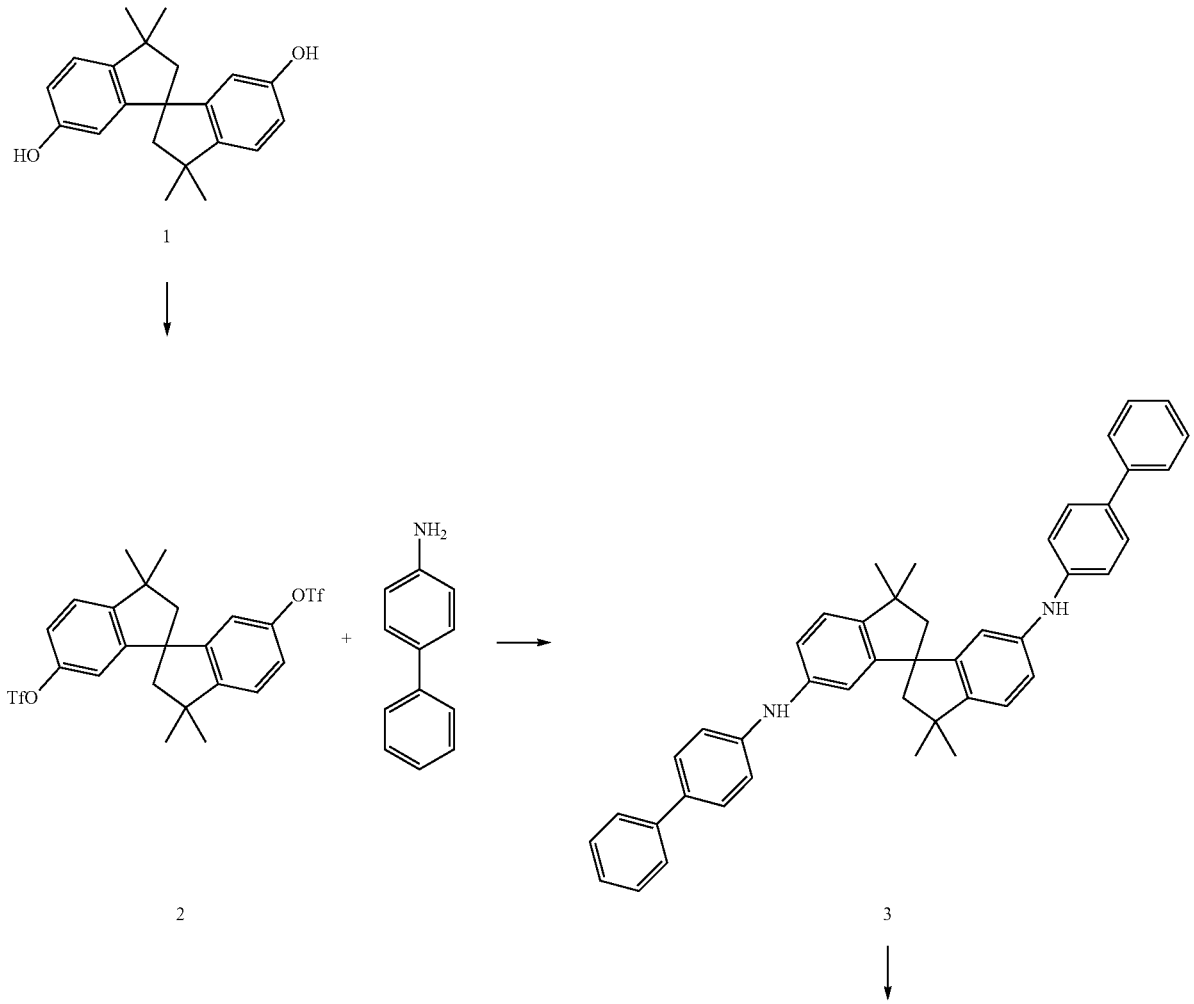

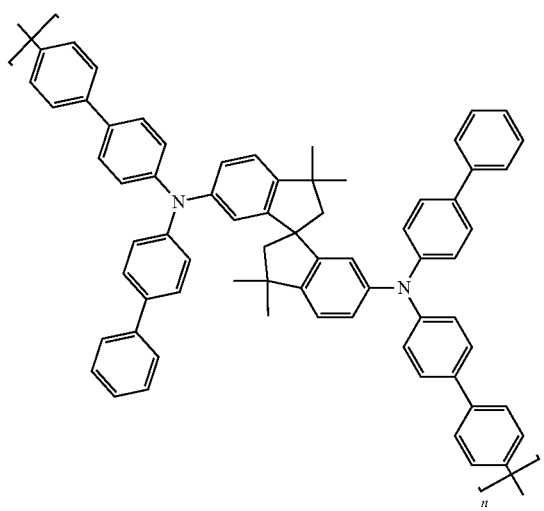

Compound D

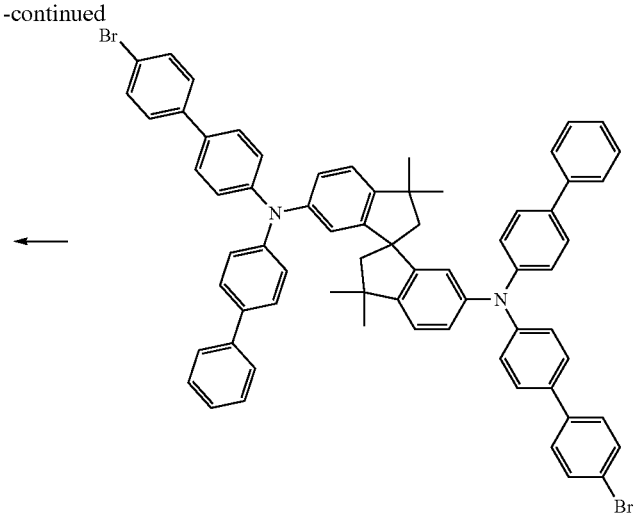

Compound C

Spiro-bisphenol 1 was synthesized following the procedure reported by Chen, W.-F.; Un, H.-Y.; Dai, S. A. *Org. Letters* 2004, 6, 2341.

Diol 1 (10.0 g, 32.4 mmol) was dissolved in 300 mL of dichloromethane and cooled to 0 C. Triflic anhydride (13.1 mL, 77.8 mmol) was slowly added and the reaction was allowed to slowly warm up to room temperature overnight. The resulting mixture was quenched with 0.5 M HCl. The layers were separated and the organic layer was washed with a sodium carbonate solution, water and then brine. Evaporation of the volatiles yielded a light pink solid in 81% yield (15 g).

Under an atmosphere of nitrogen a vial was charged with ditriflate 2 (3.07 g, 5.36 mmol), 4-aminobiphenyl (1.904 g, 11.3 mmol), $Pd_2(dba)_3$ (0.246 g, 0.268 mmol), 1,1'-bis(diphenylphosphino)ferrocene (0.297 g, 0.536 mmol) and toluene (40 mL). The resulting solution was stirred for 10 minutes followed by addition of NaO$^t$Bu (1.248 g, 13.4 mmol). The reaction was stirred at room temperature overnight followed by heating to 85° C. for 18 hrs. After cooling to room temperature, the resulting thick solution was diluted with toluene (~100 mL) and filtered through a silica pad. Evaporation of the volatiles and purification on silica using a mixture of dicholoromethane and hexane (0-40%) as the eluent yielded compound 3 in 22% yield (0.73 g).

Under an atmosphere of nitrogen a vial was charged with diamine 3 (0.73 g, 1.20 mmol), 4,4'-iodobromobiphenyl (0.902 g, 2.51 mmol), $Pd_2$ (dba)$_3$ (0.044 g, 0.048 mmol), 1,1'-bis(diphenylphosphino)ferrocene (0.053 g, 0.096 mmol) and toluene (40 mL). The resulting solution was stirred for 10 minutes followed by addition of NaO$^t$Bu (0.242 g, 2.51 mmol). The reaction was heated to 90° C. for 22 hrs. After cooling to room temperature, the resulting thick solution was diluted with toluene (~100 mL) and filtered through a silica pad. Evaporation of the volatiles and purification on silica using a mixture of dicholoromethane and hexane (40%) as the eluent yielded Compound C in 37% yield (0.479 g, 99% pure).

Compound C was polymerized using Yamamoto conditions to yield Compound D (GPO: Mn=2781, Mw=23,325).

Example 2

This example illustrates the preparation of Compound B.
The compound was made according to the following scheme.

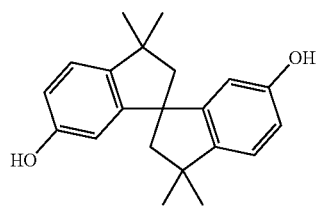

1

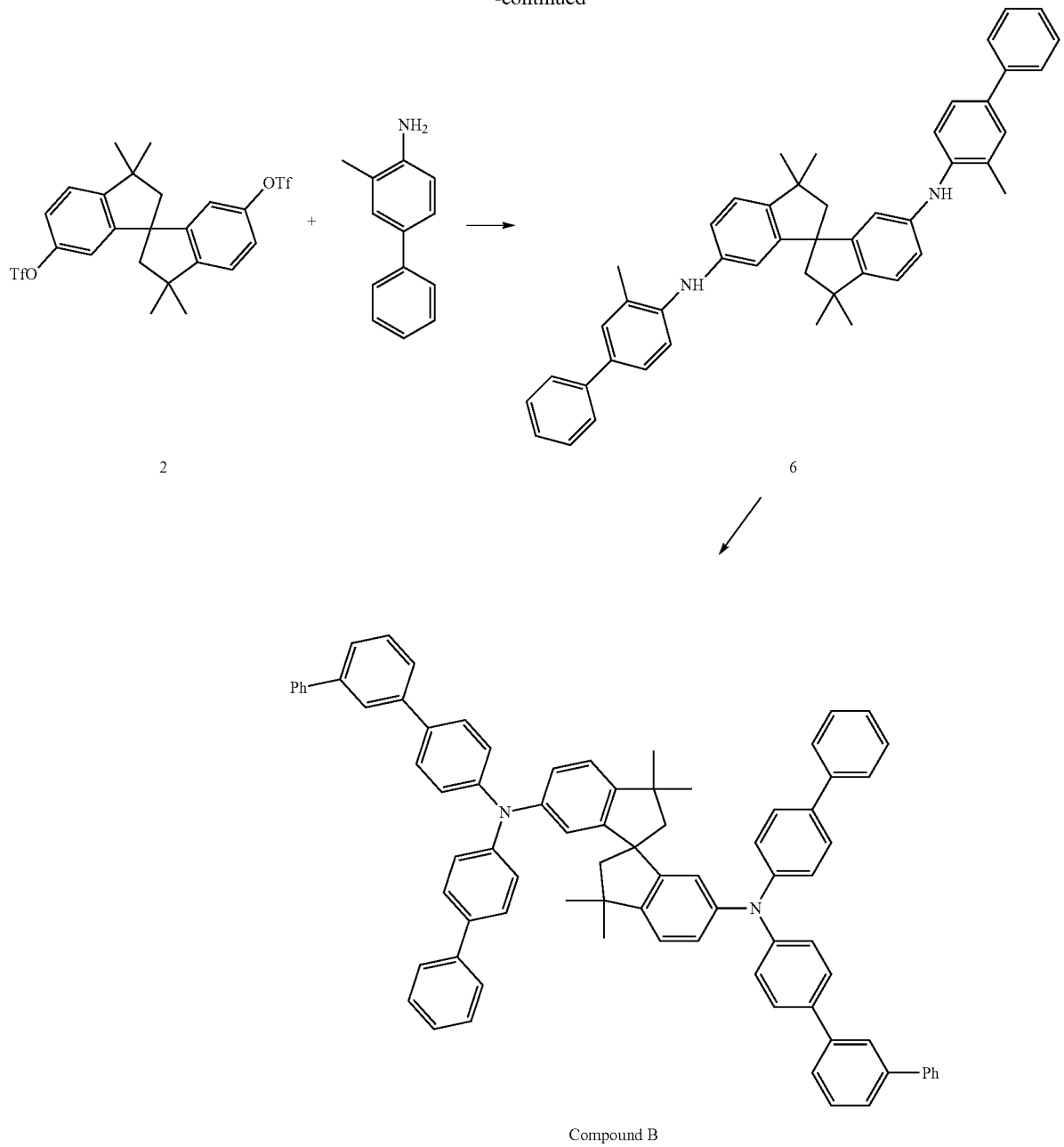

Compound B

Under an atmosphere of nitrogen a vial was charged with ditriflate 2 (1.875 g, 3.27 mmol), 3-methylbiphenyl-4-amine (1.26 g, 6.88 mmol), Pd$_2$(dba)$_3$ (0.150 g, 0.164 mmol), 1,1'-bis(diphenylphosphino)ferrocene (0.182 g, 0.327 mmol) and toluene (30 mL). The resulting solution was stirred for 10 minutes followed by addition of NaO$^t$Bu (0.762 g, 8.19 mmol). The reaction was heated to 90° C. for 18 hrs. After cooling to room temperature, the resulting thick solution was diluted with toluene (~100 mL) and filtered through a silica pad. Evaporation of the volatiles and purification on silica using a mixture of dicholoromethane and hexane (0-40%) as the eluent yielded compound 6 in 61% yield (1.28 g). Under an atmosphere of nitrogen a vial was charged with diamine 6 (1.28 g, 2.00 mmol), 4-bromo-3-methyl-3'-phenyl-biphenyl (1.943 g, 6.00 mmol), Pd$_2$(dba)$_3$ (0.044 g, 0.048 mmol), 1,1'-bis(diphenylphosphino)ferrocene (0.019 g, 0.096 mmol) and toluene (30 mL). The resulting solution was stirred for 10 minutes followed by addition of NaO$^t$Bu (0.560 g, 6.0 mmol). The reaction was heated to 90° C. for 18 hrs. After cooling to room temperature, the resulting thick solution was diluted with toluene (~100 mL) and filtered through a silica pad. Evaporation of the volatiles and purification on silica using a mixture of dicholoromethane and hexane (0-40%) as the eluent yielded Compound B in 44% yield (1.0 g).

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. The use of numerical values in the various ranges specified herein is stated as approximations as though the minimum and maximum values within the stated ranges were both being preceded by the word "about." In this manner, slight variations above and below the stated ranges can be used to achieve substantially the same results as values within the ranges. Also, the disclosure of these ranges is intended as a continuous range including every value between the minimum and maximum average values including fractional values that can result when some of components of one value are mixed with those of different value. Moreover, when broader and narrower ranges are disclosed, it is within the contemplation of this invention to match a minimum value from one range with a maximum value from another range and vice versa.

What is claimed is:
1. A compound having Formula I

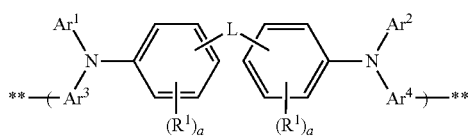

Formula I wherein:
  ** indicates a point of attachment or $R^2$;
  $Ar^1$ through $Ar^4$ are the same or different and are aryl groups;
  $R^1$ is the same or different at each occurrence and is selected from the group consisting of D, F, alkyl, aryl, alkoxy, silyl, and a crosslinkable group, where adjacent $R^1$ groups can be joined together to form an aromatic ring;

$R^2$ is the same or different at each occurrence and is selected from the group consisting of H, D, and halogen;
a is the same or different at each occurrence and is an integer from 0-4;
wherein the compound is a small molecule, an oligomer or a polymer, and wherein

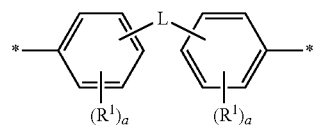

is selected from the group consisting of

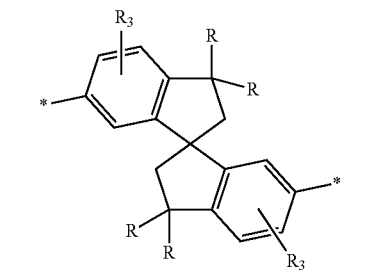

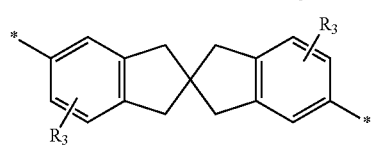

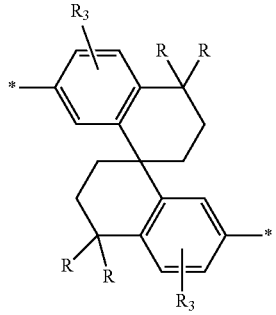

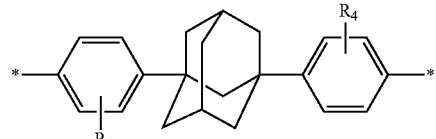 and

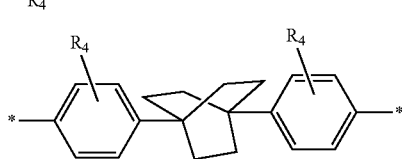

where:
  R is the same or different at each occurrence and is H or $R^1$; and
  an asterisk indicates a point of attachment to a nitrogen of an arylamino group.

2. The compound of claim 1, having Formula II

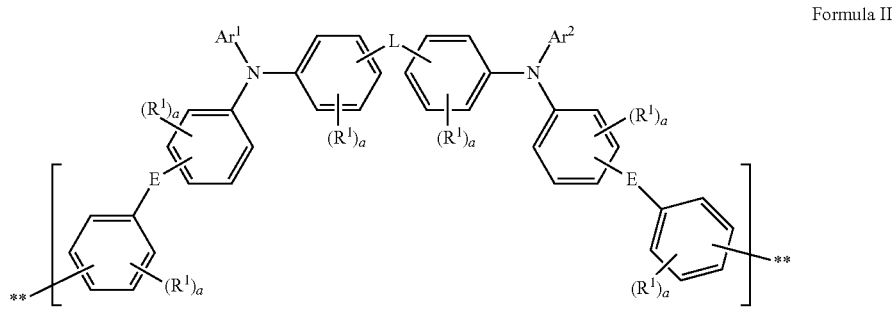

Formula II wherein:
  ** indicates a point of attachment or $R^2$;
  $Ar^1$ and $Ar^2$ are the same or different and are aryl groups;
  E is the same or different at each occurrence and is selected from the group consisting of a single bond, $C(R^3)_2$, $C(R^4)_2C(R^4)_2$, O, $Si(R^3)_2$, $Ge(R^3)_2$;
  $R^1$ is the same or different at each occurrence and is selected from the group consisting of D, F, alkyl, aryl, alkoxy, silyl, and a crosslinkable group, where adjacent $R^1$ groups can be joined together to form an aromatic ring;
  $R^2$ is the same or different at each occurrence and is selected from the group consisting of H, D, and halogen;
  $R^3$ is the same or different at each occurrence and is selected from the group consisting of H, alkyl and aryl, where adjacent $R^3$ groups can be joined together to form an aliphatic ring;
  $R^4$ is the same or different at each occurrence and is selected from the group consisting of H, D, and alkyl;
  a is the same or different at each occurrence and is an integer from 0-4;
wherein the compound is a small molecule, an oligomer or a polymer, and wherein

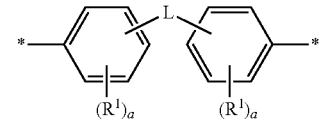

is selected from the group consisting of

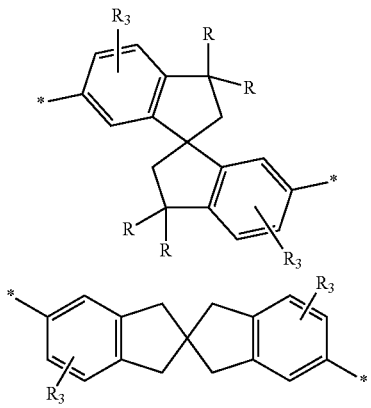

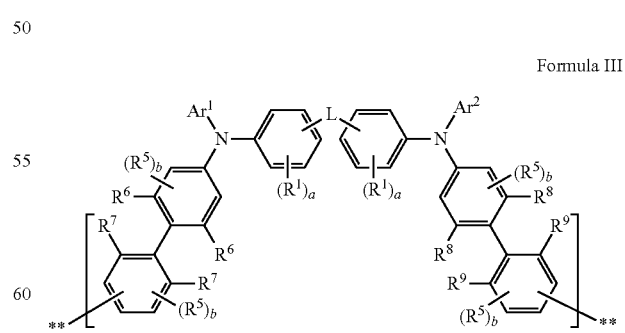

where:
  R is the same or different at each occurrence and is H or $R^1$; and
  an asterisk indicates a point of attachment to a nitrogen of an arylamino group.

3. The compound of claim 1, having Formula III

Formula III wherein:
  ** indicates a point of attachment or $R^2$;
  $Ar^1$ and $Ar^2$ are the same or different and are aryl groups;

R¹ is the same or different at each occurrence and is selected from the group consisting of D, F, alkyl, aryl, alkoxy, silyl, and a crosslinkable group, where adjacent R¹ groups can be joined together to form an aromatic ring;

R² is the same or different at each occurrence and is selected from the group consisting of H, D, and halogen;

R⁵ is the same or different at each occurrence and is selected from the group consisting of D, F, alkyl, aryl, alkoxy, silyl, and a crosslinkable group;

R⁶ through R⁹ are the same or different at each occurrence and are selected from the group consisting of H, D, F, alkyl, aryl, alkoxy, silyl, and a crosslinkable group, with the proviso that at least one of R⁶ and R⁷ is alkyl or silyl, and at least one of R⁸ and R⁹ is alkyl or silyl;

a is the same or different at each occurrence and is an integer from 0-4;

b is the same or different at each occurrence and is an integer from 0-2;

wherein the compound is a small molecule, an oligomer or a polymer, and wherein

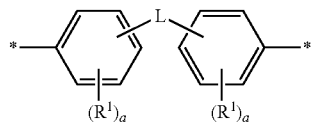

is selected from the group consisting of

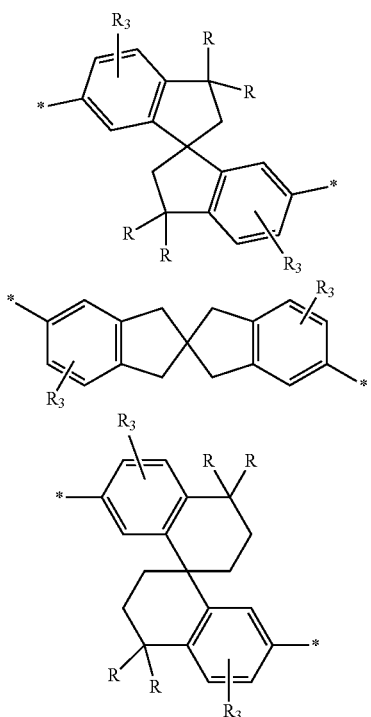

and

where:
R is the same or different at each occurrence and is H or R¹; and
an asterisk indicates a point of attachment to a nitrogen of an arylamino group.

4. The compound of claim 1, wherein Ar¹ and Ar² have Formula a

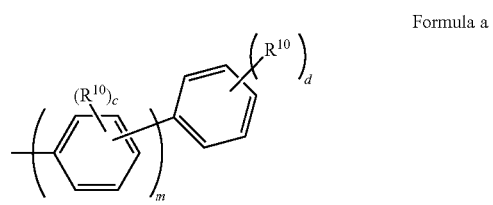

where:
R¹⁰ is the same or different at each occurrence and is selected from the group consisting of D, alkyl, alkoxy, siloxane and silyl;
c is the same or different at each occurrence and is an integer from 0-4;
d is an integer from 0-5; and
m is an integer from 1 to 5.

5. The compound of claim 1, wherein Ar¹ and Ar² are selected from the group consisting of phenyl, biphenyl, terphenyl, deuterated derivatives thereof, and derivatives thereof having one or more substituents selected from the group consisting of alkyl, alkoxy, silyl, and a substituent with a crosslinking group.

6. The compound of claim 1, wherein a=0.

7. The compound of claim 2, wherein R³ is selected from the group consisting of phenyl, biphenyl, and fluoroalkyl.

8. The compound of claim 3, wherein R⁶=R⁸=alkyl.

9. The compound of claim 3, wherein R⁷=R⁹=alkyl.

10. An organic electronic device comprising a first electrical contact layer, a second electrical contact layer and an electroactive layer therebetween, wherein the electroactive layer comprises a compound according to claim 1.

11. The device of claim 10, wherein the electroactive layer is a hole transport layer.

12. The device of claim 10, wherein the electroactive layer is an electroactive layer comprising a host compound having Formula I and a dopant.

13. The compound of claim 1, wherein

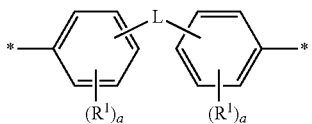

is

-continued

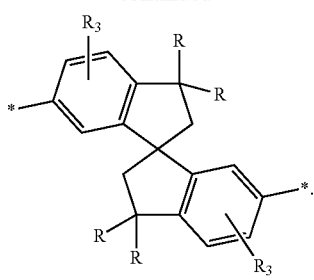

14. The compound of claim 1, wherein

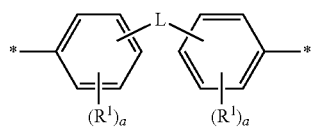

is selected from the group consisting of

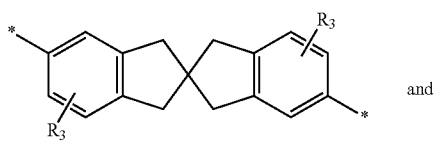

and

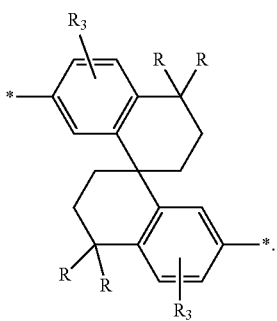

15. The compound of claim 1, wherein

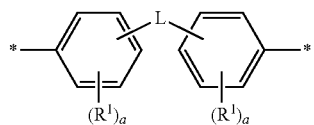

is selected from the group consisting of

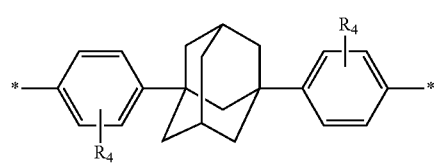

and

-continued

16. A compound having Formula I

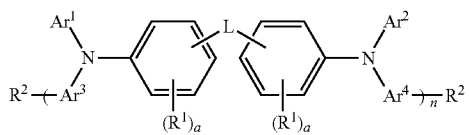

Formula I wherein:
- $Ar^1$ through $Ar^4$ are the same or different and are aryl groups;
- $R^1$ is the same or different at each occurrence and is selected from the group consisting of D, F, alkyl, aryl, alkoxy, silyl, and a crosslinkable group, where adjacent $R^1$ groups can be joined together to form an aromatic ring;
- $R^2$ is the same or different at each occurrence and is selected from the group consisting of H, D, and halogen;
- a is the same or different at each occurrence and is an integer from 0-4;
- n=1; and wherein

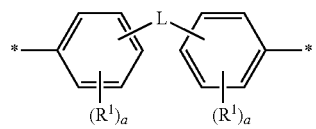

is selected from the group consisting of

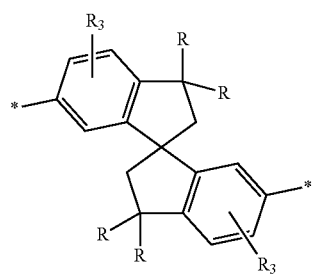

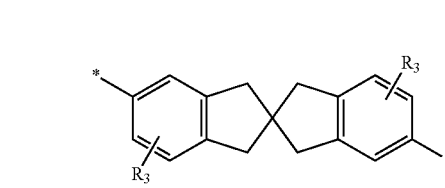

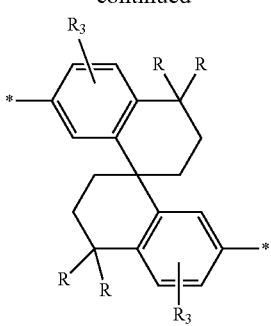

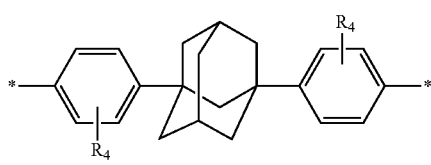 and

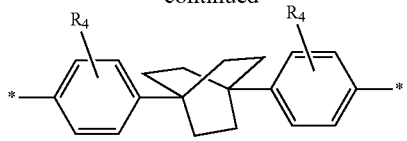

where:
R is the same or different at each occurrence and is H or $R^1$; and
an asterisk indicates a point of attachment to a nitrogen of an arylamino group.

17. The compound of claim 16, wherein $Ar^1$ and $Ar^2$ are selected from the group consisting of phenyl, biphenyl, terphenyl, deuterated derivatives thereof, and derivatives thereof having one or more substituents selected from the group consisting of alkyl, alkoxy, silyl, and a substituent with a crosslinking group.

18. The compound of claim 16, wherein a=0.

19. An organic electronic device comprising a first electrical contact layer, a second electrical contact layer and an electroactive layer therebetween, wherein the electroactive layer comprises a compound according to claim 16.

20. The compound of claim 1, wherein the compound is deuterated.

* * * * *